(12) United States Patent
Derevyagin et al.

(10) Patent No.: US 8,641,270 B2
(45) Date of Patent: Feb. 4, 2014

(54) METHOD FOR HYDROCARBON DEW POINT TEMPERATURE MEASUREMENT AND DEVICE FOR CARRYING OUT SAID METHOD

(75) Inventors: Alexandr Mikhailovich Derevyagin, Moscow (RU); Sergei Victorovich Seleznev, Saratov (RU); Alexandr Sergeevich Fomin, Petersburg (RU)

(73) Assignee: Alexandr Mikhailovich Derevyagin, Moscow (RU)

( * ) Notice: Subject to any disclaimer, the term of this patent is extended or adjusted under 35 U.S.C. 154(b) by 0 days.

(21) Appl. No.: 13/321,660

(22) PCT Filed: Jul. 15, 2009

(86) PCT No.: PCT/RU2009/000355
§ 371 (c)(1),
(2), (4) Date: Nov. 21, 2011

(87) PCT Pub. No.: WO2010/134834
PCT Pub. Date: Nov. 25, 2010

(65) Prior Publication Data
US 2012/0069866 A1    Mar. 22, 2012

(30) Foreign Application Priority Data
May 22, 2009  (RU) ................. 2009119367

(51) Int. Cl.
*G01N 25/02*    (2006.01)

(52) U.S. Cl.
USPC ............................................ 374/28; 374/16

(58) Field of Classification Search
USPC ............................................................ 374/28
See application file for complete search history.

(56) References Cited

U.S. PATENT DOCUMENTS 4,652,745 A *  3/1987  Zanardelli ................. 250/227.25
4,701,052 A * 10/1987  Schoen, Jr. ....................... 356/369

(Continued)

FOREIGN PATENT DOCUMENTS

RU    2 231 046 C1    6/2004
SU    989422 A1    1/1983

(Continued)

OTHER PUBLICATIONS

International Search Report dated Jan. 12, 2010 for Application No. PCT/RU2009/000355.

*Primary Examiner* — Lisa Caputo
*Assistant Examiner* — Jamel Williams
(74) *Attorney, Agent, or Firm* — Ladas & Parry LLP

(57) ABSTRACT

The invention relates to a field of measuring engineering.

For increase in speed, sensitivity and accuracy of measurement of a hydrocarbon dew point, a method for hydrocarbon dew point temperature measurement is provided, comprising feeding gas to be studied onto a cooled element with a condensation surface onto which a light flux is directed at an angle providing its reflection in the observation aperture, a cooling of condensation surface of a cooled element and registering the value of the light flux reflected from the condensation surface, advent of the hydrocarbon dew point being determined on the basis of the registered value, and as a material for condensation surface of a cooled element use silicon.

The device for hydrocarbon dew point temperature measurement contains a cooled element (4) with condensation surface contained in a housing (1), having openings (2) and (3) for an input and an exit of the gas to be studied, a cooler (5), the temperature sensor (6), the light source (7), located in such a manner that a light flux from it is directed after reflection from condensation surface of a cooled element (4) to the observation aperture (8) on the registrar (9) of the reflected beams, and the cooled element (4) with condensation surface is made from dielectric with refraction factor greater than refraction factor of liquid hydrocarbons.

4 Claims, 1 Drawing Sheet

(56) References Cited

U.S. PATENT DOCUMENTS

| | | | |
|---|---|---|---|
| 4,946,288 A * | 8/1990 | Siska et al. | 374/20 |
| 5,022,045 A * | 6/1991 | Elliott | 374/20 |
| 5,052,818 A * | 10/1991 | Nishizawa et al. | 374/17 |
| 5,249,856 A * | 10/1993 | Dreier | 312/238 |
| 5,804,817 A * | 9/1998 | Seiler et al. | 250/227.25 |
| 6,174,081 B1 * | 1/2001 | Holm | 374/161 |
| 7,237,946 B2 * | 7/2007 | Lindstrom et al. | 374/16 |
| 7,350,970 B2 * | 4/2008 | Derevyagin et al. | 374/28 |
| 2006/0083287 A1 * | 4/2006 | Derevyagin et al. | 374/28 |

FOREIGN PATENT DOCUMENTS

| | | | |
|---|---|---|---|
| SU | 1111088 A * | 8/1984 | |
| SU | 1679336 A1 * | 9/1991 | |

* cited by examiner

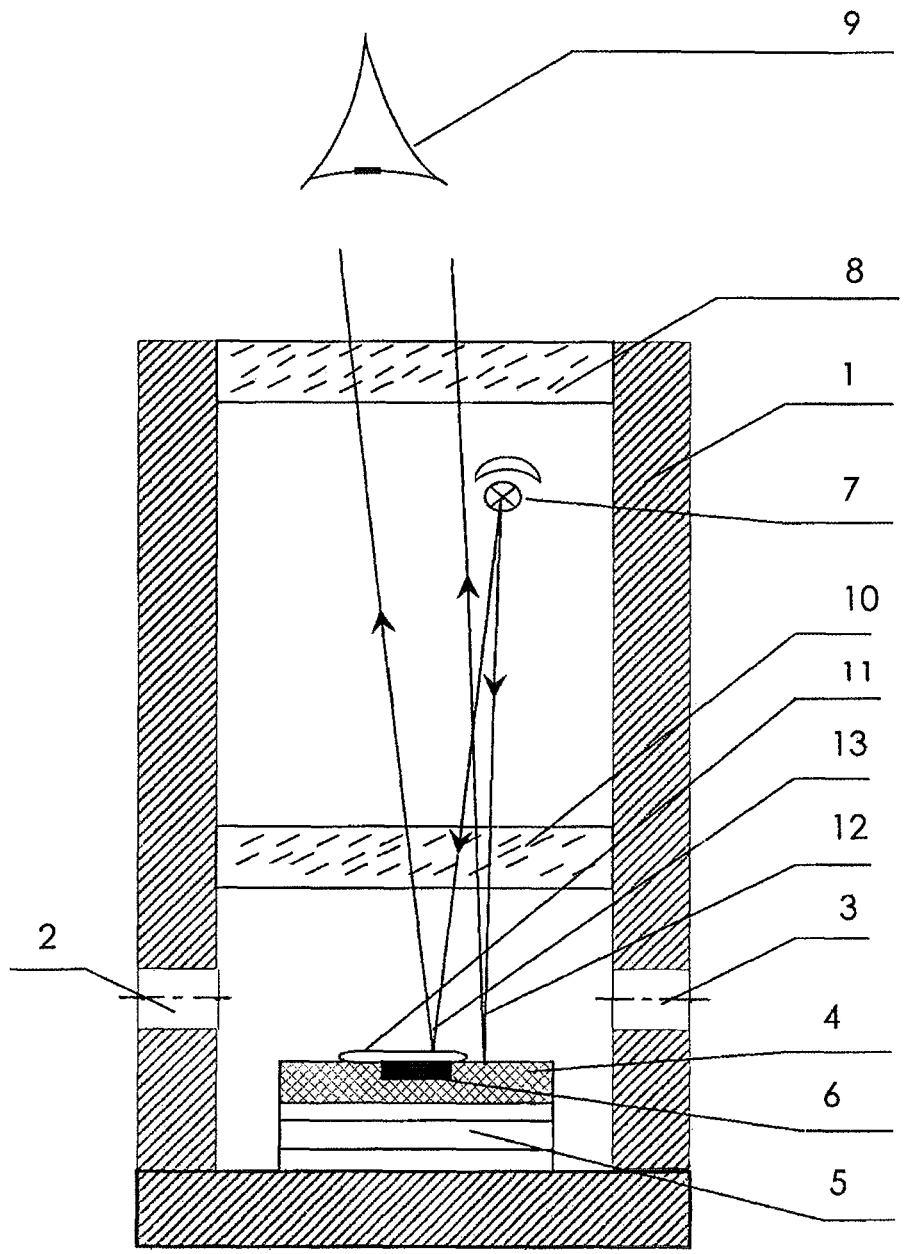

METHOD FOR HYDROCARBON DEW POINT TEMPERATURE MEASUREMENT AND DEVICE FOR CARRYING OUT SAID METHOD

FIELD OF THE INVENTION

The invention relates to a field of measuring engineering, and in particular, to the methods and devices for studying a condensation of hydrocarbon thin films of natural gas and is intended for hydrocarbon dew point definition.

PRIOR ART

Many of the known methods and devices for dew point measurement use methods based on visual observation of condensate on chilled mirror surface. Thus devices comprise a condensation mirror contacting to gas to be studied, illumination of the condensation surface is carried out by a source of visible light, a temperature of the mirror surface is measured by temperature sensor which cooling system is based on Peltier element or on gas expansion (Joule-Thomson effect). At cooling condensation mirror, visual observation over a surface of a mirror is made and at condensate occurrence a temperature of a mirror, which is dew point temperature, is fixed. However the water condensate is rather easy to find out, as it is condensed in the form of drops, while hydrocarbons in the course of condensation form the fine thin transparent film on a surface of a mirror which is difficult enough for finding out. Accordingly, sensitivity of such devices to condensation of hydrocarbon films is low, and observation and interpretation of visual formation of a film depend on literacy of the operator. Thus, it is difficult enough to provide a split-hair accuracy and repeatability of results of measurement at condensation of hydrocarbon thin films.

It is known a method for dew point measurement comprising feeding gas to be studied onto a cooled portion of an optically transparent body through which is directed a light flux, and registering a change of a light flux intensity, advent of the dew point being determined on the basis of the registered change, as well as a device for dew point measurement implemented in a given method, the device comprising the cooled portion of the optically transparent body, the portion is included in a housing and connected through light guides with radiators and a light flux transducer being connected to a register, the device comprising also a cooler and a temperature sensor (see SU patent No. 1744618, Int. Cl. G01N 25/66, published Jun. 30, 1992).

The drawback of the known technical solutions is a low reliability because of possible pollutions with admixtures of gas to be studied of the optically transparent body, because of which arise an unnecessary layer which may bring to inaccurate measurements and a loss of efficiency in operation.

The method to be closest to the proposed one by a technical essence is a method for dew point measurement, comprising feeding gas to be studied onto a cooled element with a condensation surface onto which a light flux is directed and registering the value of the light flux reflected from the condensation surface, advent of the dew point being determined on the basis of the registered value (see the RF patent No. 22085925, Int. Cl. G01N 25/08, published Jul. 20, 1995).

The drawback of the known method is a relatively low accuracy of measurement caused by a presence of a relatively long transient process when measuring.

The device to be closest to the proposed one by a technical essence is a device for dew point measurement, comprising a cooled element contained in a housing equipped with a sampling tube, the cooled element is provided with a condensation surface and is connected through an optical element to a radiator, the proposed device comprises further a register, a cooler and a temperature sensor (see the RF patent No. 22085925, Int. Cl. G01N 25/08, published Jul. 20, 1995).

The drawback of the known device is a relatively low sensitivity which decreases the accuracy of measurement since the transient process when fixing the dew point is relatively long.

Besides, the drawback of the known device is absence of the information, concerning a choice of specific type of dielectric for condensation surfaces of a cooled element. Actually, at use as dielectric, for example, a glass with refraction factor 1.5 or quartz with refraction factor 1.45, a device will not possess high sensitivity as the indicator of refraction of the concentrated liquid hydrocarbons is close to 1.45. Therefore contrast on hydrocarbon film border and glasses will be insignificant that complicates registration of the moment of hydrocarbons condensation, reduces accuracy of dew point measurement and increases transient process when fixing the dew point. Besides, it is difficult enough to provide repeatability of results of measurement at condensation of hydrocarbon thin films.

DISCLOSURE OF THE INVENTION

In a basis of the invention is stated a task of increasing the speed, sensitivity and accuracy of measurement of a hydrocarbon dew point.

This task is solved by the fact that in a method for hydrocarbon dew point temperature measurement, comprising feeding gas to be studied onto a cooled element with a condensation surface onto which a light flux is directed at an angle providing its reflection in the observation aperture, cooling condensation surface of a cooled element and registering the value of the light flux reflected from the condensation surface, advent of the hydrocarbon dew point being determined on the basis of the registered value, and as a material for condensation surface of a cooled element use silicon-dielectric with refraction factor greater than refraction factor of liquid hydrocarbons.

According to other invention, the device for measurement of hydrocarbon dew point temperature contains a cooled element with condensation surface contained in a housing with the transparent window, having openings for an input and an exit of the gas to be studied, a cooler, the temperature sensor, the light source located in such a manner that a light flux from it is directed after reflection from condensation surface of a cooled element through the observation aperture on the registrar of the reflected beams, and the cooled element with condensation surface is made from silicon, and the housing is supplied by the transparent partition, dividing its internal volume on a gas part in which are located a cooled element with condensation surface, a cooler, the temperature sensor and openings, and a part in which the light source and the observation aperture are placed.

The essence of inventions consists that performance of condensation surfaces of a cooled element from a dielectric material with high refraction factor in comparison with refraction factor of liquid hydrocarbons allows to provide sensitivity substantial growth to occurrence of condensed impurity and accuracy of measurement of a hydrocarbon dew point.

Besides, speed of process of measurement raises.

Preliminary tests allow to judge possibility of wide industrial application.

FIG. 1 illustrates a structure of the claimed device which carries out proposed method.

BEST OPTION OF THE EMBODIMENT OF THE INVENTION

A method for hydrocarbon dew point temperature measurement, comprising feeding gas to be studied onto a cooled element with a condensation surface onto which a light flux is directed at an angle providing its reflection in the observation aperture. Then a cooling of condensation surface of a cooled element is provided and registering the value of the light flux reflected from the condensation surface, advent of the hydrocarbon dew point being determined on the basis of the registered value, and as a material for condensation surface of a cooled element use silicon-dielectric with refraction factor greater than refraction factor of liquid hydrocarbons.

The device for hydrocarbon dew point temperature measurement contains a cooled element (4) with condensation surface contained in a housing (1), having openings (2) and (3) for an input and an exit of the gas to be studied, a cooler (5), the temperature sensor (6), the light source (7), located in such a manner that a light flux from it is directed after reflection from condensation surface of a cooled element (4) through the optical system of observation aperture (8) on the registrar (9) of the reflected beams. The cooled element (4) with condensation surface is made from silicon-dielectric with refraction factor greater than refraction factor of liquid hydrocarbons.

The housing (1) is supplied by the transparent partition (10), dividing its internal volume on a gas part in which are located a cooled element (4) with condensation surface, a cooler (5), the temperature sensor (6) and openings (2) and (3), and a part in which the light source (7) and the observation aperture (8) are placed.

The Device Operates in the Following Manner

The gas to be studied is fed onto a cooled element (4) with a condensation surface onto which a light flux is directed at a defined angle and registers the value of the light flux reflected from the condensation surface through the observation aperture (8).

In the presence of condensed admixtures in the gas to be studied on the condensation surface of the cooled element (4) at a defined temperature are formed a layer of condensate which significantly changes the intensity of the reflected beams. In this moment a temperature sensor (6) records the temperature value of condensation mirror.

It should be noted herewith that the registration of the light flux takes place even at an insignificant appearance of the condensate on the condensation surface of the cooled element (4). This defines the high sensitivity of the device and therefore the accuracy of measurement.

The improvement of the method and device consists in use of dielectric material with high reflection factor as a material for condensation surface (condensation mirror) of the cooled element. The source (7) of visible lights placed in the housing (1), provides illumination of condensation surfaces through glass—the transparent partition (10), being a part of a measuring cell, under the small angle guaranteeing the hit of reflected light in the aperture (8) of optical systems. As a result, at cooling condensation surface (condensation mirror) of the cooled element supplied with the temperature sensor (6), cooling system—a cooler (5) to temperature of formation of a thin film of a condensate—liquid hydrocarbons (11), on a dielectric surface appears well visible to the registrar (9) reflected beams (to the observer or a video camera) the visual effect, caused by change of reflection factor of a beam (12) from a mirror without a condensate and a beam (13) from a condensate film.

Thus, in the proposed inventions is achieved the stated technical result increasing of speed, sensitivity and accuracy of measurement of a hydrocarbon dew point.

INDUSTRIAL APPLICABILITY

The described advantages of the proposed technical solutions ensure them the possibility of wide industrial usage in the field of the measurement engineering for the measurement of dew point temperature at studying hydrocarbon thin films condensation of the natural gas.

The invention claimed is:

1. A method for hydrocarbon dew point temperature measurement, comprising:
    feeding a gas to be studied onto a cooled element with a condensation surface onto which a light flux is directed at an angle providing its reflection in the observation aperture,
    cooling the condensation surface of the cooled element,
    registering condensation surface images caused by change of reflection factor of a beam from the condensation surface without a condensate and a beam from a condensate film,
    determining on the basis thereof the advent of the hydrocarbon dew point,
    where in order to increase the sensitivity to occurrence of condensed impurity and accuracy of measurement of a hydrocarbon dew point, a dielectric material with a refraction factor higher than that of liquid hydrocarbons is used as a material for the condensation surface.

2. The method according to claim 1, wherein silicon is used as a material for the condensation surface.

3. A device for hydrocarbon dew point temperature measurement, comprising:
    a housing (1) containing a cooled element (4) with a condensation surface, a cooler (5), a temperature sensor (6), a light source (7), and an observation aperture (8), the housing (1) having openings (2) and (3) for an input and an exit of a gas to be studied;
    wherein the light source (7) is located in such a manner that a light flux from the light source (7) is directed after reflection from the condensation surface of the cooled element (4) and from a condensate film through the observation aperture (8) to a registrar (9) of condensation surface images,
    wherein the cooled element (4) with the condensation surface is made from dielectric material with a refraction factor higher than that of liquid hydrocarbons, and the housing (1) which is supplied by a transparent partition (10), dividing its internal volume on a gas part in which are located the cooled element (4) with the condensation surface, the cooler (5), the temperature sensor (6) and openings (2) and (3), and a part, insulated from the gas, in which the light source (7) and the observation aperture (8) are placed.

4. The device according to claim 3, wherein silicon is used as a material for the condensation surface.

* * * * *